United States Patent [19]

Zeugner et al.

[11] Patent Number: 4,497,740
[45] Date of Patent: Feb. 5, 1985

[54] 2-AZIDOMETHYL-1,4-BENZODIAZEPINE COMPOUNDS

[75] Inventors: Horst Zeugner, Hanover, Fed. Rep. of Germany; Dietmar Römer, Allschwil, Switzerland; Hans Liepmann, Hanover; Wolfgang Milkowski, Burgdorf, both of Fed. Rep. of Germany

[73] Assignee: Kali-Chemie Pharma GmbH, Hanover, Fed. Rep. of Germany

[21] Appl. No.: 386,303

[22] Filed: Jun. 8, 1982

[30] Foreign Application Priority Data

Jun. 19, 1981 [DE] Fed. Rep. of Germany ....... 3124013

[51] Int. Cl.³ .................. C07D 401/04; C07D 403/04; C07D 405/04; C07D 409/04
[52] U.S. Cl. .......................... 260/244.4; 260/239 BD; 260/239.3 D; 260/245.7; 260/330.3; 260/330.8; 260/330.9; 260/465 D; 260/465 E; 546/272; 546/298; 548/537; 549/72; 549/365; 549/439; 549/483; 560/142; 564/220; 564/344; 564/355; 424/244; 424/263; 424/274; 424/275; 424/282; 424/285
[58] Field of Search .............. 260/244.4, 330.3, 330.9, 260/245.7, 239 BD; 424/274, 263, 275, 285, 282

[56] References Cited

U.S. PATENT DOCUMENTS

| Re. 28,315 | 1/1975 | Schmitt | 260/239.3 D |
|---|---|---|---|
| 3,398,159 | 8/1968 | Berger et al. | 260/239.3 D |
| 3,546,212 | 12/1970 | Felix et al. | 260/239.3 D |
| 3,560,482 | 2/1971 | Yamamoto et al. | 260/239.3 D |
| 3,998,809 | 12/1976 | Milkowski et al. | 260/239 BD |
| 4,096,141 | 6/1978 | Milkowski et al. | 260/239 BD |
| 4,098,786 | 7/1978 | Milkowski et al. | 260/239 BD |
| 4,244,869 | 1/1981 | Milkowski et al. | 260/239 BD |
| 4,325,957 | 4/1982 | Zeagner et al. | 260/330.9 |
| 4,368,159 | 1/1983 | Walser et al. | 260/244.4 |

FOREIGN PATENT DOCUMENTS 2314993 10/1974 Fed. Rep. of Germany .
2353160 11/1974 Fed. Rep. of Germany .
2353187 11/1974 Fed. Rep. of Germany .
2436147 2/1975 Fed. Rep. of Germany .

OTHER PUBLICATIONS

"Structure–Activity Relationships in the 1,4-Benzodiazepine Series": *Drugs Affecting the Central Nervous System*, pp. 237–240, 244–245, 256, 262.

Primary Examiner—Alton D. Rollins
Attorney, Agent, or Firm—Schwartz, Jeffery, Schwaab, Mack, Blumenthal & Koch

[57] ABSTRACT

New 2-acylaminomethyl-1H-2,3-dihydro-1,4-benzodiazepine compounds are described having the general formula I

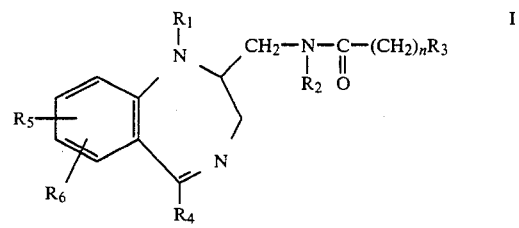

wherein $R_1$ is a hydrogen atom or a lower alkyl or alkenyl radical or the cyclopropylmethyl radical, $R_2$ is a hydrogen atom, or a lower alkyl or alkenyl radical, n is 0, 1 or 2, $R_3$ is an optionally substituted furyl, thienyl, pyrrolyl, pyridyl or phenyl radical, $R_4$ is an optionally substituted furyl, thienyl, pyrrolyl or pyridyl radical, $R_5$ is a hydrogen or halogen atom, or a lower alkyl, lower alkoxy, hydroxyl, lower alkylthio, nitro, trifluoromethyl, cyano, amino, lower mono- or dialkylamino, lower monoalkanoylamino, lower N-alkyl-N-alkanoylamino or lower alkanoyloxy radical, and $R_6$ is a hydrogen atom, or a lower alkyl or lower alkoxy radical or $R_5$ and $R_6$ together denote a methylenedioxy or ethylenedioxy radical. The compounds have pharmacological, for example, analgesic, properties.

1 Claim, No Drawings

2-AZIDOMETHYL-1,4-BENZODIAZEPINE COMPOUNDS

BACKGROUND OF THE INVENTION

This invention relates to new 2-acylaminomethyl-5-heteroaryl-1H-2,3-dihydro-1,4-benzodiazepine compounds and their salts, to pharmaceutical compositions containing these compounds and to processes for the preparation of these compounds, as well as to intermediates used for preparing these compounds.

German Offenlegungsschrift No. 2,353,187 describes, inter alia, 2-acylaminomethyl-1,4-benzodiazepines in which the acyl radical is a low molecular weight alkanoyl radical. These substances primarily have an anticonvulsive action.

SUMMARY OF THE INVENTION

It is the object of the present invention to provide new 2-acylaminomethyl-1,4-benzodiazepine compounds having valuable pharmacological properties as well as a process and novel intermediate compounds for preparing and pharmaceutical compositions incorporating such new 2-acylaminomethyl-1,4-benzodiazepine compounds.

This and other objects of the invention are achieved by providing a 2-acylaminomethyl-1H-2,3-dihydro-1,4-benzodiazepine compound corresponding to the general formula I

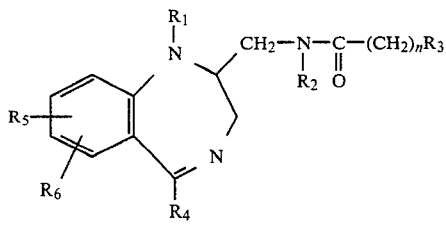

wherein
$R_1$ is hydrogen, lower alkyl, lower alkenyl, or cyclopropylmethyl;
$R_2$ is hydrogen, lower alkyl, or lower alkenyl;
n is 0, 1 or 2;
$R_3$ is

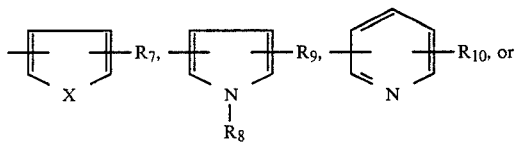

a    b    c

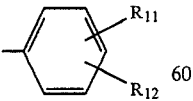

d wherein
X is oxygen or sulfur;
$R_7$ is hydrogen, halogen, lower alkyl, lower alkoxy or nitro;
$R_8$ is hydrogen or lower alkyl;
$R_9$ is hydrogen or lower alkyl;
$R_{10}$ is hydrogen, chlorine, or lower alkyl;
$R_{11}$ is hydrogen, halogen, lower alkyl, lower alkoxy, hydroxyl, lower alkylthio, nitro, trifluoromethyl, cyano, amino, lower mono- or dialkylamino, lower monoalkanoylamino, lower N-alkyl-N-alkanoylamino or lower alkanoyloxy;
$R_{12}$ is hydrogen, halogen; lower alkyl, lower alkoxy, hydroxyl or lower alkanoyloxy; or
$R_{11}$ and $R_{12}$ are bonded to adjacent carbon atoms and together denote methylenedioxy or ethylenedioxy;
$R_4$ is one of the radicals a, b, or c defined above;
$R_5$ is hydrogen, halogen, lower alkyl, lower alkoxy, hydroxyl, lower alkylthio, nitro, trifluoromethyl, cyano, amino, lower mono- or dialkylamino lower monoalkanoylamino, lower N-alkyl-N-alkanoylamino or lower alkanoyloxy; and
$R_6$ is hydrogen, halogen, lower alkyl or lower alkoxy; or
$R_5$ and $R_6$ are bonded to adjacent carbon atoms and together denote methylenedioxy or ethylenedioxy;
and the optical isomers and acid addition salts of said compound.

In a further aspect of the invention, the objects are achieved by providing a process for preparing a 2-acylaminomethyl-1H-2,3-dihydro-1,4-benzodiazepine compound corresponding to the general formula I

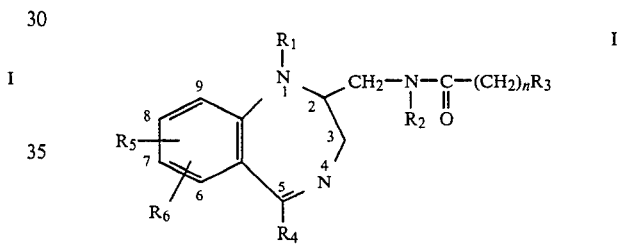

wherein $R_1$, $R_2$, $R_3$, $R_4$, $R_5$, $R_6$ and n have the meanings defined above, an optical isomer or acid addition salt thereof, comprising acylating a 2-aminomethyl-1H-2,3-dihydro-1,4-benzodiazepine compound corresponding to the formula II

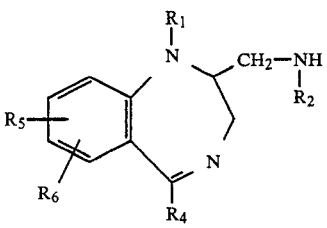

wherein $R_1$, $R_2$, $R_4$, $R_5$ and $R_6$ have the meanings defined above with a compound corresponding to the formula III $R_3—(CH_2)_n—CO—Y$

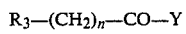

wherein
$R_3$ and n have the meanings defined above; and
Y is hydroxyl or a radical which can be eliminated by aminolysis; and
if the product is to be an optical isomer, separating a racemic mixture of the product of the acylation reaction into its optical isomers and, if the product is to be an acid addition salt, reacting the product of the acylation reaction with a suitable acid.

In still other aspects of the invention, the objects are achieved by providing new compounds corresponding to the general formulas II

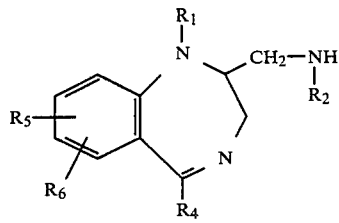

and IV

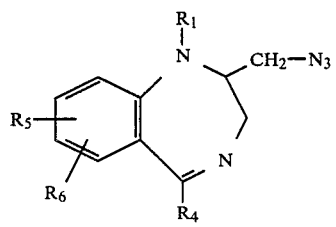

wherein $R_1$, $R_2$, $R_4$, $R_5$ and $R_6$ are as described above and by providing a pharmaceutical composition comprising a pharmacologically active amount of a 2-acylaminomethyl-1,4-benzodiazepine as described above and at least one pharmaceutically acceptable carrier.

It has now been found that the present 2-acylaminomethyl-5-heteroaryl-1,4-benzodiazepine compounds have a valuable pharmacological action, in particular an analgesic action, and a favourable profile of action with good therapeutic range and low toxicity.

As used herein, the terms lower alkyl, lower alkenyl, lower alkoxy and lower alkanoyl are intended to denote radicals containing up to four carbon atoms.

DETAILED DESCRIPTION OF PREFERRED EMBODIMENTS

The present invention provides a 2-acylaminomethyl-1H-2,3-dihydro-1,4-benzodiazepine compound of the general formula I

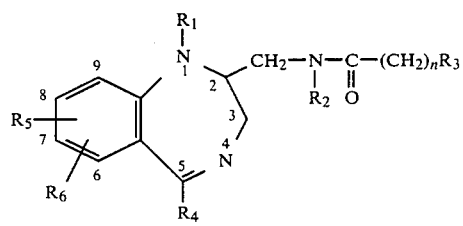

wherein
$R_1$ is a hydrogen atom, or a lower alkyl or alkenyl radical or the cyclopropylmethyl radical;
$R_2$ is a hydrogen atom or a lower alkyl or alkenyl radical;
n is 0, 1, or 2;
$R_3$ is one of the following radicals a, b, c, or d

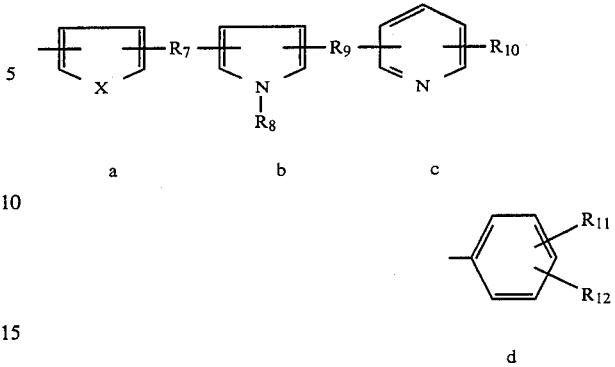

wherein X is an oxygen or sulphur atom, $R_7$ is a hydrogen or halogen atom, or a lower alkyl, lower alkoxy or nitro radical, $R_8$ is a hydrogen atom or a lower alkyl radical, $R_9$ is a hydrogen atom or lower alkyl radical, $R_{10}$ is a hydrogen or chlorine atom, or a lower alkyl radical, $R_{11}$ is a hydrogen or halogen atom, or a lower alkyl, lower alkoxy, hydroxyl, lower alkylthio, nitro, trifluoromethyl, cyano, amino, lower mono- or dialkylamino, lower monoalkylanoylamino, lower N-alkyl-N-alkanoylamino or lower alkanoyloxy radical, $R_{12}$ is a hydrogen or halogen atom, or a lower alkyl, lower alkoxy, hydroxyl or lower alkanoyloxy radical, or $R_{11}$ and $R_{12}$ are bonded to adjacent carbon atoms and together denote a methylenedioxy or ethylenedioxy radical,
$R_4$ is one of the radicals a, b, or c defined above,
$R_5$ is hydrogen or halogen atom, or a lower alkyl, lower alkoxy, hydroxyl, lower alkylthio, nitro, trifluromethyl, cyano, amino, lower mono- or dialkylamino, lower monoalkylamino, lower N-alkyl-N-alkanoylamino or lower alkanoyloxy radical, and $R_6$ is a hydrogen or halogen atom, or a lower alkyl or lower alkoxy radical, or $R_5$ and $R_6$ are bonded to adjacent carbon atoms and together denote a methylenedioxy or ethylenedioxy radical, and the optical isomers and acid addition salts of said compounds.

If, in the compounds of the formula I, the substituents $R_5$ and $R_6$ of the phenylene ring or the substituents $R_7$ to $R_{12}$ contained in the radicals $R_3$ and $R_4$ contain a lower alkyl radical, the latter can be linear or branched and preferably contains 1 to 4 carbon atoms. Suitable examples of such radicals include methyl, ethyl, n-propyl, isopropyl, n-butyl, 1-methylpropyl, 2-methylpropyl and tert.-butyl radicals, preferably methyl, ethyl, n-propyl and isopropyl radicals. In particular when the phenyl rings are di- or trisubstituted, ethyl and in particular methyl are preferred substituents. Preferred lower alkoxy and lower alkylthio substituents are methoxy and methylthio radicals.

Possible lower alkyl and alkenyl radicals which may be represented by $R_1$ and $R_2$ are those which have up to 4 carbon atoms and which are linear or branched, and include, for example methyl, ethyl, propyl, isopropyl, n-butyl, 1-methylpropyl, 2-methylpropyl, tert.-butyl, allyl, 2-butenyl and 3-butenyl radicals. $R_1$ is preferably a hydrogen atom or a lower alkyl or cyclopropylmethyl radical, more preferably a lower alkyl radical, and most preferably the methyl radical. $R_2$ is preferably a hydrogen atom.

Suitable halogen atoms for the substituents $R_5$ and $R_6$ include fluorine, chlorine and bromine atoms, and the substituents $R_5$ and $R_6$ are preferably located in the 7- and/or 8-positions. If $R_5$ is an alkylthio, nitro, trifluoromethyl, cyano or optionally substituted amino radical, $R_6$ is preferably a hydrogen atom. In the case of halogen and/or alkyl or halogen and/or alkoxy substituents, mono- or disubstitution is advantageous.

In the case where $R_3$ is a phenyl group d which may be optionally substituted with the radicals $R_{11}$ and/or $R_{12}$, what was stated above for the substituents $R_5$ and $R_6$ also applies to the substituents $R_{11}$ and $R_{12}$.

If $R_3$ and/or $R_4$ is a radical a where X is an oxygen atom, $R_7$ is preferably a hydrogen atom or a lower alkyl or nitro radical, preferably a hydrogen atom or methyl radical. If $R_3$ and/or $R_4$ is a radical a where X is a sulphur atom, $R_7$ is preferably a hydrogen atom, a lower alkyl radical, more preferably the methyl radical, a halogen atom, more preferably a chlorine or bromine atom, or a nitro or lower alkoxy radical.

If $R_3$ and/or $R_4$ is a pyrrolyl group b, $R_8$ is preferably a hydrogen atom or a methyl radical and $R_9$ is preferably a hydrogen atom or methyl radical.

The groups a to c can be bonded at their 2- or 3-position, preferably at their 3-position, to the benzodiazepine structure.

If $R_3$ and/or $R_4$ represent a pyridyl group c, $R_{10}$ is preferably a hydrogen atom, but if $R_{10}$ is a lower alkyl radical, it is preferably the methyl radical.

According to another aspect of the invention there is provided a process for preparing a new 2-acylaminomethyl-1H-2,3-dihydro-1,4-benzodiazepine compound of the general formula I an optical isomer or acid addition salt thereof, wherein a 2-aminomethyl-1H-2,3-dihydro-1,4-benzodiazepine compound of the formula II

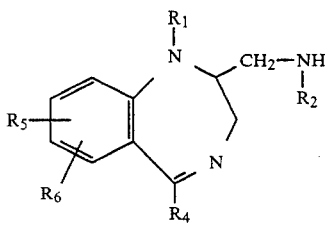

wherein $R_1$, $R_2$, $R_4$, $R_5$ and $R_6$ have the above defined meanings, is acylated with an acid or reactive acid derivative of the formula III $R_3$—$(CH_2)_n$—CO—Y     III where $R_3$ and n have the meanings herein defined and Y is a hydroxyl radical or a radical which can be eliminated by aminolysis to give a resulting compound of the formula I; whereafter if $R_2$ in the resulting compound is a hydrogen atom, the resulting compound may be alkylated to give a compound of the formula I where $R_2$ is a lower alkyl or alkenyl radical, and/or if $R_5$, $R_{11}$ and/or $R_{12}$ in the resulting compound is/are a lower alkanoyloxy or lower alkanoylamino radical, these radicals are hydrolysed to give free hydroxyl or amino radicals, and wherein, if appropriate, a racemic mixture of the compound of formula I is separated into its optical isomers and, if appropriate, a free compound of formula I is converted into its acid addition salt or an acid addition salt is converted into the free compound of formula I.

The acylation of the aminomethyl compound of formula II can be carried out by methods which are in themselves customary for forming amide groupings by aminoacylation. Suitable acylating agents which may be used include acids of the formula IIIa $R_3$—$(CH_2)_n$—CO—OH     IIIa wherein $R_3$ and n have the above defined meanings, or reactive derivatives of such acids. Suitable reactive derivatives are in particular acid halides, preferably acid chlorides, acid esters and acid anhydrides, for example compounds of the formula III wherein the radical Y, which can be eliminated by aminolysis, is a halogen atom, in particular a chlorine or bromine atom, or a lower alkoxy radical, in particular an alkoxy radical having 1 to 4 carbon atoms, or an O—CO—Z radical where Z is an $R_3(CH)_n$— or lower alkyl or alkoxy radical. The acylation can be carried out, in a solvent which is inert under the reaction conditions, at a temperature of from −30° C. to the boiling point of the solvent, under atmospheric pressure or under an elevated pressure. Suitable solvents include halogenated hydrocarbons, such as methylene chloride or chloroform, aromatic hydrocarbons, such as benzene, toluene, xylene or chlorobenzene, cyclic ethers, such as tetrahydrofuran or dioxane, ketones, such as, for example, acetone or methyl isobutyl ketone, or dimethylformamide, or mixtures of these solvents.

The acylation, in particular if the acylating agent used is a carboxylic acid halide or carboxylic acid anhydride, may also be carried out in the presence of an acid-binding agent. Suitable acid-binding agents include inorganic bases, in particular alkali metal carbonates and alkali metal hydroxides, such as, for example, sodium carbonate, potassium carbonate and potassium hydroxide, or organic bases, in particular tertiary lower alkylamines and pyridines, such as, for example, triethylamine, tripropylamine, tributylamine, pyridine, 4-dimethylaminopyridine or 4-pyrrolidinopyridine. Organic bases used in excess can simultaneously also serve as solvents.

If the acylating agent used is the acid itself or an ester, the reaction of the amino compound of formula II with the acid of formula IIIa or with its ester is advantageously carried out in the presence of a coupling agent known in peptide chemistry as suitable for amide formation. Examples of suitable coupling agents which promote amide formation with free acids by reacting in situ with the acid to form a reactive acid derivative include alkylcarbodiimides, preferably cycloalkylcarbodiimides, such as dicyclohexylcarbodiimide, carbonyldiimidazole and N-(lower alkyl)-2-halopyridinium salt, in particular halides or tosylates, preferably N-methyl-2-chloropyridinium iodide (see for example Mukaiyama in Angew.Chemie 91 789–812). The reaction in the presence of a coupling agent can advantageously be carried out at a temperature of from −30° to +30° C. in the presence of a solvent such as a halogenated hydrocarbon and/or aromatic solvent, and optionally in the presence of an acid-binding amine. Examples of suitable coupling agents which promote amide formation with esters by forming a reactive derivative of the amino compound include tri-(lower alkyl)-aluminiums, in particular trimethylaluminium, which are suitable for activating the reaction of the amino compounds with esters, and phosphorus trichloride. Suitable inert solvents for the reaction in the presence of trialkylaluminium include aromatic hydrocarbons and/or halogenated hydrocarbons. The reaction of the amino compound with the trialkylaluminium is preferably carried out at a temperature of from −20° C. to room temperature, and the subsequent reaction of the monoalkylaluminium-azo compound formed as an intermediate with the ester can be carried out at a temperature between room temperature and the boiling point of the solvent. Further coupling agents which are suitable for the present amide formation and are also used in peptide syntheses, are described, for example in "Advanced Organic Chemistry" by Jerry March, McGraw-Hill Ltd., 2nd Edition, pages 382 to 388, and in "The Chemistry of Amides" by Jacob Zabicky, 1970, Interscience Publishers John Wiley and Sons, London, Chapter 2: "Synthesis of Amides".

If the substituents $R_3$, $R_4$, $R_5$ and/or $R_6$ contain free hydroxyl or amino radicals, these radicals can be provided, if desired, before the acylation with a protective group which can be eliminated after the reaction, for example by hydrolysis. The free amino, monoalkylamino and hydroxyl radicals can be protected, for example, as sulphinylimino, acetylalkylamino or acetoxy radicals, which can readily be eliminated. If free unprotected phenolic hydroxyl radicals are present, some of these can also be acylated in the acylation, but the phenol-ester groups which result can be readily and selectively split hydrolytically, for example by treatment with sodium carbonate solution.

If $R_3$ and/or $R_4$ represent a pyrrole ring, it is advantageous to carry out the acylation under mild reaction conditions, for example in the presence of one of the abovementioned coupling agents.

The resulting compounds of the formula I wherein $R_2$ is a hydrogen atom can, if desired, be subsequently alkylated in a manner which is in itself known to give the corresponding N-alkyl compounds. Suitable alkylating agents include alkyl halides, alkyl-sulphates and alkyl-sulphonates. Advantageously, the amido compound of formula II is initially reacted with a metalating agent, such as, for example, an alkali metal hydride, alkali metal amide, alkali metal alcoholate, an organic lithium compound or a thallium(I) alcoholate, in an inert solvent, and the metalated compound can subsequently be reacted with the alkylating agent. The reaction can be carried out at a temperature of from −80° C. to the boiling point of the solvent, and suitable metalating agents include, in particular, sodium hydride, lithium butyl, lithium phenyl, sodium amide, lithium diisopropylamide, a sodium alkoxide or a thallium(I) alkoxide. Depending upon the metalating agent used, suitable solvents include open and cyclic ethers, such as diethyl ether, tetrahydrofuran or dioxane, aromatic hydrocarbons, such as benzene or toluene, dimethylformamide, dimethyl sulphoxide or, if the metalating agent is a metal alcoholate, also the corresponding alcohols, namely methanol in the case of methoxides and ethanol in the case of ethoxides.

The present compounds of the general formula I are obtained by the present process in the form of their racemates. The present invention encompasses not only the racemic mixtures but also the optically active forms of the compounds of the formula I. The optically active compounds can be separated from the racemic mixtures in a manner which is in itself known such as by reaction with a suitable optically active acid, such as, for example, tartaric acid, O,O'-dibenzoyltartaric acid, mandelic acid, di-O-isopropylidene-2-oxo-L-gulonic acid, and subsequent fractional crystallisation of the resulting salts into their optically active antipodes (see for example Tetrahedron 33 (1977) pages 2725–2736).

Separation into the optically active compounds can, if desired, also be carried out in a suitable preliminary stage.

The compounds of the formula I can be isolated from the reaction mixture and purified using conventional procedures. Acid addition salts can be converted in a customary manner into the free bases and the latter can be converted, if desired, in a known manner into acid addition salts, preferably into salts with pharmacologically acceptable acids.

Compounds of the general formula IIa

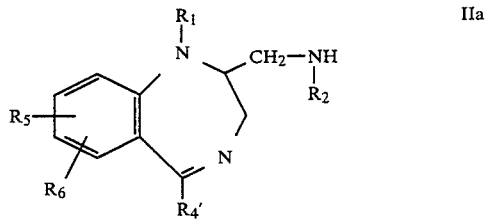

wherein $R_1$, $R_2$, $R_5$ and $R_6$ have the above defined meanings and $R_4'$ represents one of the following groups a', b or c

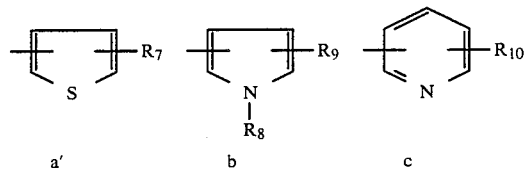

a'  b  c where $R_7$, $R_8$, $R_9$ and $R_{10}$ have the above defined meanings, are new valuable intermediate products for the preparation of pharmacologically active compounds, for example of compounds of the formula I. Compounds of the formula II can be obtained from compounds of formula IV

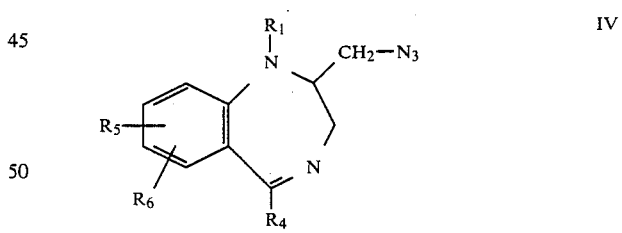

where $R_1$, $R_5$, $R_6$ and $R_4$ have the above defined meanings, by reducing the azido groups to the amino group, or from compounds of the formula V

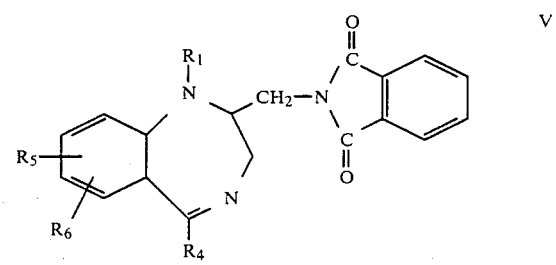

where $R_1$, $R_5$, $R_6$ and $R_4$ have the above defined meanings, by hydrolysing the phthalimide group to the amino group, thereby resulting in compounds of formula IIb

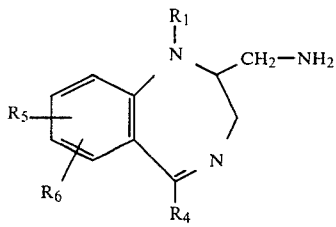     IIb where $R_1$, $R_5$, $R_6$ and $R_4$ have the above defined meanings, whereafter the compounds of formula IIb can, if desired, be alkylated in conventional manner.

The reductive cleavage of compounds of formula IV can be carried out in a manner which is in itself known by means of reducing agents known for the reduction of azides.

Examples of suitable reducing agents include hydrazine hydrate/Raney nickel, 1,3-dimercaptopropane and tin(II) chloride. The reduction by means of hydrazine hydrate/Raney nickel is advantageously carried out in an inert solvent, for example in a lower alcohol, under basic catalysis, for example with the addition of a tertiary amine, for example a lower alkylamine, such as triethylamine, preferably at room temperature. The reduction by means of dimercaptopropane is also carried out in an inert solvent, if appropriate under basic catalysis. Examples of suitable solvents for this purpose include lower alcohols, dimethylformamide and pyridine/water. The reduction by means of tin(II) chloride is advantageously carried out in concentrated hydrochloric acid.

The phthalimide compounds of formula V can be hydrolysed in conventional manner, either under acid conditions, for example with the addition of dilute hydrochloric acid, or under alkaline conditions, for example with the addition of hydrazine hydrate, in water or in a mixture of water and a water-soluble organic solvent, preferably a lower alcohol, at a temperature of from 20° to 120° C., preferably at the boiling temperature of the reaction mixture.

The compounds of the formula IIb can be alkylated by methods which are in themselves customary for aminoalkylation, for example by reaction with an alkyl halide, alkyl-sulphate or alkyl-sulphonate or by reductive alkylation.

The compounds of formula II can also be obtained by reacting a compound of formula IX and/or a compound of the formula X

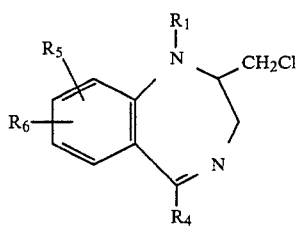     IX

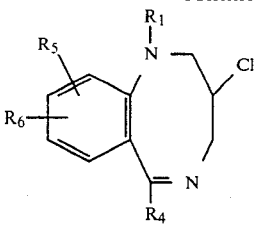     X wherein $R_1$, $R_5$, and $R_6$ and $R_4$ have the above defined meanings with an amine of the formula XI $R_2NH_2$     XI wherein $R_2$ has the above defined meaning.

The reaction of a compound of formula IX and/or X, preferably a mixture of the isomeric compounds IX and X, with ammonia or primary lower alkylamine such as, for example, methylamine, ethylamine, propylamine, butylamine or allylamine, is carried out in a manner which is in itself known at a temperature of from 20° to 150° C., preferably at the boiling temperature of the reaction mixture. An excess of the amine can also serve as the solvent. If desired, an inert solvent can also be added, for example a lower alcohol, such as methanol, ethanol, isopropanol or tert-butanol, a cyclic ether, such as dioxane or an aromatic hydrocarbon, such as benzene, toluene or xylene. If desired, ammonia or the primary amine can be replaced by an alkali metal salt thereof in the reaction with the compound of formula IX and/or X. The solvent used in this case is preferably an excess of the particular amine or liquid ammonia. However, it is also possible to add other inert solvents, for example cyclic ethers or aromatic hydrocarbons. The alkali metal salts of the amine can be formed in situ or can be added in a solid form. The temperature for the reaction can vary from −50° to +150° C.

The compounds of formula IV have not hitherto been described in the literature. They are new, valuable intermediate products for the preparation of pharmacologically active compounds, for example of compounds of formula I. Moreover, they themselves have valuable pharmacological properties. In particular, they have properties characteristic of sedative and psychotropic agents.

According to yet another aspect of the present invention, a compound of formula IV can be obtained by reacting a compound of formula IX and/or a compound of the formula X with an alkali metal azide.

The reaction can be effected by methods customary for azide formation. For example a compound of formula IX and/or X, in particular a mixture of the isomeric compounds of the formulae IX and X, is or are reacted with an alkali metal azide, preferably sodium azide or potassium azide, in an inert solvent at a temperature of from −30° to 150° C. Examples of suitable solvents include halogenated hydrocarbons, such as methylene chloride or chloroform, cyclic ethers, such as tetrahydrofuran or dioxane, dimethylformamide, dimethyl sulphoxide, hexamethylphosphoric triamide, lower alcohols, such as methanol, ethanol or tert.-butanol, and lower ketones, such as acetone or methyl isopropyl ketone.

The compounds of formula IV can be isolated from the reaction mixture and purified in conventional manner. However, these compounds can also be further reacted without further purification, if necessary after removal of the solvent. The free compounds of the formula IV can be converted in conventional manner into their acid addition salts and vice versa.

If desired, racemic mixtures of compounds of formula IV can be separated into their optical isomers in a manner which is in itself known.

A compound of formula V can be obtained by reacting a compound of formula IX and/or a compound of the formula X with an alkali metal phthalimide. The reaction is advantageously carried out in an inert solvent, for example a lower alcohol, such as methanol, ethanol or isopropanol, a cyclic ether, such as dioxane, or dimethylformamide, at a temperature of from 50° to 130° C. If desired, potassium iodide can be added as a catalyst.

The compounds of formula IX, and X, which are used as starting substances, can be prepared in a manner which is in itself known. For example, compounds wherein $R_4$ denotes a radical a as defined above can be obtained by the methods described in German Offenlegungsschriften Nos. 2,221,558 and 2,353,187.

In particular, a 2-hydroxy-1,3-diaminopropane of the general formula VI

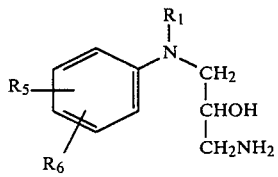

VI wherein $R_1$, $R_5$ and $R_6$ have the above defined meanings can be acylated by means of an acyl chloride of formula VII

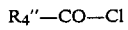   VII where $R_4''$ denotes a radical a as defined above to give an acylamine of the general formula VIII

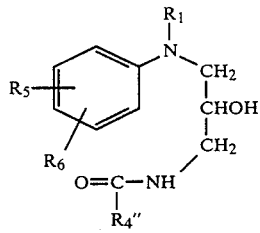

VIII wherein $R_1$, $R_4''$, $R_5$ and $R_6$ have the above defined meanings and the resulting compound of formula VIII can subsequently be cyclised in a manner which is in itself known by reaction with a phosphorus oxyhalide, preferably phosphorus oxychloride. For this purpose, a compound of formula VIII or an acid addition salt thereof is advantageously treated, as described in German Offenlegungsschrift No. 2,520,937, with phosphorus oxychloride at a temperature of from 100° to 150° C., preferably at the boiling temperature of the reaction mixture. This results in the formation of a mixture of the two isomeric compounds IX and X which mixture can be isolated from the reaction mixture in a manner which is itself known.

The two isomeric compounds IX and X are present in the isomeric mixture in varying amounts, depending on the nature of the substituents $R_4''$, $R_5$ and $R_6$. However, this is immaterial as far as the subsequent reaction of this mixture is concerned, since the two isomers react in uniform reaction to give a compound of the general formula II or a compound of the general formula IV or V. Tedious separation or analysis of the mixture of isomers is thus not necessary before further reaction. However, it is of course possible, if desired, to employ the isomers also at this stage separately and singly for the subsequent reactions.

In order to prepare a compound of the formula IX, where $R_4$ denotes a radical a, as defined above, it is also possible to start with a 2-amino-benzoyl compound of the formula XII

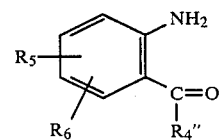

where $R_4''$, $R_5$ and $R_6$ have the above defined meanings. This compound is first reacted with epichlorohydrin to give a compound of the formula XIIIa

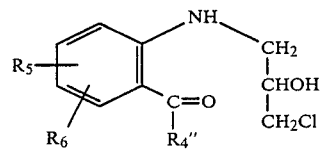   XIIIa where $R_4''$, $R_5$ and $R_6$ have the above defined meanings, and, if desired, the amino group in these compounds can subsequently be alkylated in a manner which is itself known. The alkylation can be effected, for example by the methods, known from the literature, of reductive carbonylamination, for example by reaction with a lower aldehyde in the presence of a reducing agent, preferably formic acid. The resulting compounds of the formula XIII

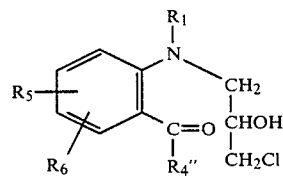   XIII wherein $R_1$, $R_4''$, $R_5$ and $R_6$ have the above defined meanings, are subsequently converted by treatment with sodium hydroxide solution into the corresponding epoxide compounds which are cyclised, by heating for several hours together with ammonia in an inert solvent, for example a lower alcohol such as methanol, to give benzodiazocine compounds of the formula XIVa

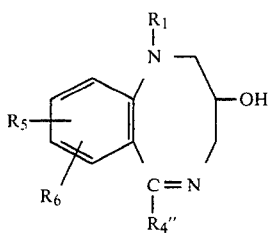

XIVa wherein $R_1$, $R_4''$, $R_5$ and $R_6$ have the above defined meanings. The compounds of formula XIVa can be converted by treatment with thionyl chloride ($SOCl_2$), for example by boiling $SOCl_2$ under reflux, into the benzodiazepine compounds of formula IX. This process is particularly suitable for preparing those compounds where $R_4$ represents thiophene.

In order to prepare a compound of formula IX or X, or a mixture of such compounds, it is also possible to start from an anthranilate or anthranilic nitrile of the formula XV

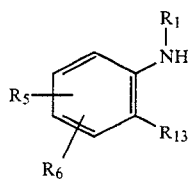

XV where $R_1$, $R_5$ and $R_6$ have the above defined meanings and $R_{13}$ is a lower alkoxy carbonyl radical or a nitrile (CN) radical. The compound is first reacted with epichlorohydrin to give a compound of the formula XVI

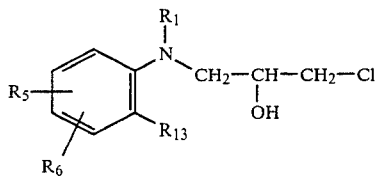

XVI where $R_1$, $R_5$, $R_6$ and $R_{13}$ have the above defined meanings, which is then cyclised to give a lactone or iminolactone of the formula XVII

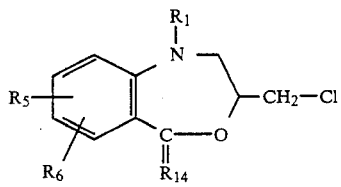

XVII wherein $R_1$, $R_5$ and $R_6$ have the above defined meanings and $R_{14}$ is an oxygen atom or imino radical, the cyclisation being effected for example by treatment with finely ground potassium hydroxide in ether. Epoxides which correspond to the compounds of the formula XVI are formed under these reaction conditions as byproducts, but they can be reconverted into compounds of the formula XVI by treatment with hydrochloric acid. Iminolactones of the formula XVII ($R_{14}$=NH), obtained from nitriles, are subsequently converted by hydrolysis into the corresponding lactones ($R_{14}$=O). The lactones of the formula XVII are reacted with metallised compounds obtained in situ by reacting a compound of the formula XVIII $$R_4-Br \qquad XVIII$$

wherein $R_4$ has the above defined meaning with lithium butyl to give a compound of the formula XIX

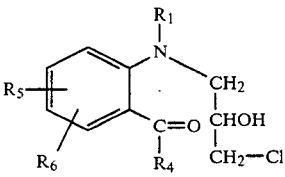

XIX wherein $R_1$, $R_4$, $R_5$ and $R_6$ have the above defined meanings. These compounds are converted by reaction with an alkali metal phthalimide and subsequent hydrolysis of the phthalimide radical to an amino radical into compounds of the formula XX

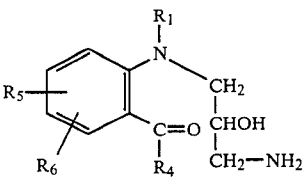

XX wherein $R_1$, $R_4$, $R_5$ and $R_6$ have the above defined meanings. The latter compounds are cyclised by heating for several hours at a temperature of from 80° to 100° C. in an inert solvent, for example an aromatic hydrocarbon, such as toluene, to give a benzodiazocine compound of the formula XIV

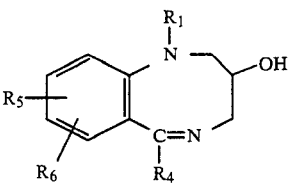

XIV wherein $R_1$, $R_4$, $R_5$ and $R_6$ have the above defined meanings. The compounds of formula XIV can be converted by treatment with triphenylphosphine/carbon tetrachloride/methylene chloride into a mixture of the isomeric compounds of formula IX and X.

Provided the substituents in the benzodiazepine structure do not contain alkyloxy or alkylthio radicals, a starting material of formula II where $R_1$ is a hydrogen atom can also be obtained by dealkylating a compound of formula II where $R_1$ is an alkyl, preferably methyl, radical, in a manner which is in itself known, by means of hydriodic acid. The reaction can be carried out in concentrated hydriodic acid at a temperature of from 50° to 100° C.

The present 2-acylaminomethyl-5-heteroaryl-1H-2,3-dihydro-1,4-benzodiazepine compounds and their pharmacologically acceptable salts are distinguished from previously known 1,4-benzodiazepine derivatives by a novel type of pharmacological action profile an they show, in particular, marked analgesic properties, in addition to psychopharmacological, diuretic and antiarrhythmic effects with low toxicity.

Because of their marked analgesic properties, the present compounds are useful analgesics.

The analgesic properties of the compounds are exhibited in pharmacological tests on small rodents and on monkeys. Thus, it is possible to demonstrate that the compounds of formula I are able to raise the pain threshold of mammals. This is particularly demonstrated in two standard pharmacological test methods, the tail flick test on the mouse and the arthritis pain test on the rat.

Description of the pharamacological methods of investigation.

1. Determination of the minimum toxic dose.

Maximum doses of 300 mg/kg. of the test substance are administered orally to male mice of 20-25 g. weight. The animals are observed carefully for toxicity symptoms for 3 hours. In addition, all symptoms and cases of death are recorded for a period of 24 hours after administration. Accompanying symptoms are also observed and recorded. If death or toxic symptoms are observed, decreasing doses are administered to additional mice until no more toxic symptoms occur. The lowest dose which induces toxic symptoms is reported as the minimum toxic dose.

2. Arthritis pain test on the rat.

Male rats of the strain OFA with a weight of 160-180 g. are anaesthetised by administration of 20 mg./kg. i.p. of phenobarbital sodium. 0.1 ml. of a suspension of *Mycobacterium Smegmae* (S1043) in paraffin oil (0.6 mg. of Mycobact./0.1 ml. of oil) are injected intracutaneously into the left rear paw. 14 days later, when a marked secondary arthritis has developed, particularly in the right rear paw, the effects of the test substances are investigated. 30 minutes before administration of the test substances, a control measurement in undertaken in which the ankle joint of the right rear paw is flexed three times and the number of sounds given out is counted. Rats which do not react are eliminated. 3 hours after oral dosage of the test substance, the flexion procedure is repeated. Animals which either give out sound only once or not at all are regarded as being protected against pain. Between 9 and 20 rats are used per dose and the $ED_{50}$ (95% confidence range) is determined by the method of Litchfield and Wilcoxon) (1949). The $ED_{50}$ is designated as that dose which produces protection in 50% of the animals treated.

3. Tail flick ray test on the mouse

The method is based on the procedure described by D'Amour and Smith (1941). However, non-fasting male and female mice having body weights of 16-25 g. are used instead of rats. 30 minutes before treatment with the test substance, each mouse is placed alone in a cylindrical vessel such that it cannot turn round and move forward. Its tail, lying in a narrow groove, projects out of the vessel. A particular point on the tail of each animal (at about 35 mm. from the root of the tail) is subjected to the radiant heat from a lamp of known intensity and temperature which is situated directly beneath the tail. The time in seconds required by the mouse to flick the tail out of the ray of light is determined twice, once 30 and once 15 minutes before subcutaneous administration of the test substance (10 mg./kg.). The mice for which the reaction times deviate by more than 25% are eliminated. The reaction times are again measured 15 and 30 minutes after treatment and an increase in the reaction times of more than 75% of the average values before treatment of the same mouse is regarded as an analgesic effect. The $ED_{50}$ (95% confidence range) of each test substance 30 minutes after administration is regarded as that dose which increases the reaction time before treatment by more than 75% in 50% of the animals. The calculation is carried out in accordance with the method of Litchfield and Wilcoxon (1949).

The compounds of the formula I show analgesic effects in the pharmacological tests described above in a dose range of 0.1-100 mg./kg.

The following Table I represents the results obtained by the test methods described above.

The Example numbers given for the compounds of the formula I relate to the preparation Examples given below.

TABLE I

| Test substance of the formula I Example No. | Inhibition of the arthritis pain in rat $ED_{50}$ mg./kg. p.o. | Tail flick test on the mouse $ED_{50}$ mg./kg. s.c. | Minimum toxic dose in the mouse mg./kg. p.o. |
|---|---|---|---|
| 11 | ~2 | 2.8 | 300 |
| 7 | 8.5 | | |
| 6 | 2 | | 300 |
| 1 | >32 <56 | 1 | 200 |
| 5 | ~10 | 2.7 | 300 |
| 12 | 32 | | >300 |
| 13 | >32 <56 | 10 | 200 |
| 84 | 18 | | >300 |
| 87 | >18 <32 | 2.6 | |
| 88 | >18 <32 | 8.3 | |
| 89 | 10 | | |

Both the free bases and their pharmacologically acceptable acid addition salts can be employed as drugs. Suitable acid addition salts are the salts of those acids, the anions of which are not toxic at suitable dosages, that is to say the acid addition salts are preferably salts with pharmacologically acceptable acids. Suitable acids which may be used for salt formation with compounds of general formula I include, for example, hydrochloric acid, hydrobromic acid, sulphuric acid, phosphoric acid, methanesulphonic acid, ethanesulphonic acid, benzenesulphonic acid, p-toluenesulphonic acid, citric acid, acetic acid, lactic acid, succinic acid, maleic acid, fumaric acid, malic acid, tartaric acid, benzoic acid, phenylacetic acid and mandelic acid.

The compounds of the formula I can be administered in customary pharmaceutical forms which contain about 0.1 to 100 mg. of active substance per single dose. The dosage used is, of course, adjusted to the species to be treated and to the individual requirements. However, in general analgesic effects are obtained in test animals with doses of from 0.1 to 100 mg./kg. For the treatment of pain in humans and larger mammals, preparations with, for example, 0.25 to 50 mg., particularly 1 to 50 mg., of active substance per single dose are suitable. Parenteral formulations will generally contain less active substance than oral preparations.

The compounds of the formula I can be employed alone or in combination with pharmaceutically suitable excipients and/or auxiliaries in the form of solid or liquid dosage forms. Examples of solid preparations which my be administered orally, include tablets, capsules, powders, granules or coated tablets, and examples of other solid preparations include suppositories. Solid preparations can contain customary pharmaceutical inorganic excipients such as talc and/or organic excipients such as lactose or starch in addition to customary pharmaceutical auxiliaries, for example lubricants such as magnesium stearate. Liquid preparations, such as solutions, suspensions or emulsions can contain the customary diluents such as water, oils, petroleum jelly and/or suspension agents such as polyoxyethylene glycol and the like. In addition, other auxiliaries can also be added such as, for example, preservatives, stabilisers and wetting agents.

The following non-limiting examples illustrate the preparation of the novel compounds of the general formula I and also of the hitherto unknown novel intermediate products.

In Table II below, any amounts of water, acetone, ethanol or the like included in salt forms are stated.

EXAMPLE 1

1-Methyl-2-[(furan-3-carbonyl)-aminomethyl]-5-(3'-thienyl)-1H-2,3-dihydro-1,4-benzodiazepine (A) 42.6 g. of $N_1$ (thiophene-3-carbonyl)-$N_2$-methyl-$N_2$-phenyl-2-hydroxy-1,3-diaminopropane were boiled for 5 hours under reflux in 126 ml. of phosphorus oxychloride. The reaction solution was then discharged onto a mixture of 250 mg. of ice/250 ml. of concentrated hydrochloric acid and 250 ml. of methylene chloride. The methylene chloride phase was separated off, washed several times with water and was then washed with 30% strength soidum hydroxide solution until any acid constituents had been removed. The phase was then again washed with water till neutral, dried over sodium sulphate and filtered, and methylene chloride was evaporated in vacuo. The residue obtained was 31.5 g. of a mixture of the two isomeric compounds 1-methyl-2-chloromethyl-5-(3'-thienyl)-1H-2,3-dihydro-1,4-benzodiazepine and 1-methyl-3-chloro-6-(3'-thienyl)-1,2,3,4-tetrahydro-1,5-benzodiazocine.

(B) The above mixture was dissolved in 230 ml. of methanol and boiled under reflux for 12 hours together with 21.6 g. of potassium phthalimide and 6 g. of potassium iodide. The methanol was then distilled off in vacuo, and the residue was taken up in methylene chloride and filtered, and the filtrate was again evaporated. The residue was filtered with toluene and methylene chloride through 300 g. of alumina of activity level I. 30.9 g. of 1-methyl-2-phthalimidomethyl-5-(3'-thienyl)-1H-2,3-dihydrobenzodiazepine were obtained.

(C) The above phthalimide compound was heated for 4 hours under reflux together with 8.7 g. of hydrazine hydrate in 300 ml. of ethanol. The solution was filtered, and the solvent was distilled off in vacuo. The residue was taken up in dilute hydrochloric acid (20%) and again filtered. The filtrate was then extracted with methylene chloride, and concentrated sodium hydroxide solution was then added to the acidic, aqueous solution until it showed an alkaline reaction. The precipitated base was dissolved in methylene chloride, and the solution was washed with saturated sodium chloride solution until neutral, dried over sodium sulphate and filtered. The solvent was then distilled off, and the residue (13.4 g.) was dissolved in ether, and a solution of hydrogen chloride in ether was added to the solution. The precipitated crystals of 1-methyl-2-aminomethyl-5-(3'-thienyl)-1H-2,3-dihydro-1,4-benzodiazepine dihydrochloride were filtered off with suction and thoroughly washed with ethyl acetate and ether. Melting point: 188°–207° C. (with decomposition), yield: 16.9 g.

(D) 10.9 g. of the above hydrochloride were suspended in 130 ml. of methylene chloride, and 14.3 ml. of triethylamine were added to the suspension. 4.5 g. of furan-3-carbonyl chloride in 50 ml. of methylene chloride were slowly added dropwise while cooling with ice. After the dropwise addition, the reaction solution was stirred for 2 hours at room temperature. The solution was then washed with water, with ammonia solution (10%), and again with water and sodium chloride solution, dried over sodium sulphate and filtered. The solvent was then distilled off in vacuo. The remaining 1-methyl-[2-[(furan-3-carbonyl)-aminomethyl]-5-(3-thienyl)-1H-2,3-dihydro-1,4-benzodiazepine was dissolved in ether/ethyl acetate 1:1 and a solution of hydrogen chloride in ether was added to the solution. The precipitated crystals of hydrochloride were then filtered off with suction and recrystalled from acetone. Melting point of the hydrochloride: 200°–202.5° C. Yield: 7.9 g.

EXAMPLE 2

1-Methyl-2-[(furan-2-carbonyl)-aminomethyl]-5-(2'-furyl)-1H-2,3-dihydro-1,4-benzodiazepine (A) 273 g. of $N_1$-furan-2-carbonyl-$N_2$-methyl-$N_2$-phenyl-2-hydroxy-1,3-diaminopropane were boiled for 1.5 hours under reflux in 810 ml. of phosphorus oxychloride. When the reaction was complete, the bulk of the phosphorus oxychloride was distilled off (about 750 ml.), and the residue was discharged onto 500 g. of ice, and 500 ml. of methylene chloride were added. The organic phase was separated off and repeatedly washed with water. The cyclisation product was then liberated as a base by the addition of concentrated sodium hydroxide solution. Customary working up produced 249 g. of crude product in the form of the base. This crude base was dissolved in 750 ml. of ether, and the solution was filtered, whereafter a solution of hydrogen chloride in ether was added to the filtrate. The precipitated crystals of the hydrochloride of the cyclisation product were filtered off with suction. The crystals were dissolved in water, and the base was again obtained by the addition of concentrated sodium hydroxide solution. This base was dissolved in ether, and the solution was washed with water, dried over sodium sulphate and filtered. After the solvent had been distilled off, 179.9 g. of an oily residue were obtained, which consisted of a mixture of 1-methyl-2-chloromethyl-5-(2'-furyl)-1H-2,3-dihydro-1,4-benzodiazepine and 1-methyl-3-chloro-6-(2'-furyl)-1,2,3,4-tetrahydro-1,5-benzodiazocine.

(B) Without separation or further purification, 179.9 g. of the above mixture were boiled for 12 hours under reflux together with 130 g. of potassium phthalimide and 36 g. of potassium iodide in 1,200 ml. of methanol. The methanol was then distilled off, and the residue was taken up in 500 ml. of methylene chloride. After the addition of 50 g. of γ-alumina, the mixture was stirred for 4 hours. The solution was then filtered with suction from the residue, and the filtrate was evaporated. 1-Methyl-2-phthalimido-5-(2'-furyl)-1H-2,3-dihydro-1,4-benzodiazepine (211.4 g.), obtained as an oily crude product, was employed without further purification in the next reaction stage.

(C) 38.5 g. of 1-methyl-2-phthalimido-5-(2'-furyl)-1H-2,3-dihydro-1,4-benzodiazepine were boiled under reflux for 7.5 hours together with 140 ml. of hydrochloric acid (24%). The reaction solution was filtered, and the filtrate was extracted with methylene chloride (100 ml.). Concentrated sodium hydroxide solution was then added to the acidic, aqueous phase until it had an alkaline reaction, and the phase was then extracted with methylene chloride. The methylene chloride phase was washed with water, dried over sodium sulphate and filtered, and the filtrate was evaporated in vacuo. The amine compound (18.5 g.) remaining as residue was dissolved in ether, and a solution of hydrogen chloride in ether was added to the solution. 1-Methyl-2-aminomethyl-5-(2'-furyl)-1H-2,3-dihydro-1,4-benzodiazepine dihydrochloride precipitated in the form of orange-coloured crystals, which were filtered off, stirred with warm acetone, filtered off with suction and dried. Melting point: 210° C. Yield: 2.8 g.

(D) 32.8 g. of 1-methyl-2-aminomethyl-5-(2'-furyl)-1H-2,3-dihydro-1,4-benzodiazepine dihydrochloride were suspended in 450 ml. of methylene chloride, and 46 ml. of triethylamine were added to the suspension. 14.4 g. of furan-2-carboxylic chloride in 50 ml. of methylene chloride were added while cooling with ice. Customary working up isolated the 1-methyl-2-[(furan-2-carbonyl)aminomethyl]-5-(2'-furyl)-1H-2,3-dihydro-1,4-benzodiazepine in the form of its hydrochloride. Melting point: 239°-241° C. (with decomposition), yield: 17 g.

EXAMPLE 3

1-Methyl-2-[(thiophene)-2-carbonyl)-aminomethyl]-5-(2'-thienyl)-1H-2,3-dihydro-1,4-benzodiazepine (A) 203 g. of $N_1$-(thiophene-2-carbonyl)-$N_2$-methyl-$N_2$-phenyl-2-hydroxyl-1,3-diaminopropane were boiled under reflux for 20 hours in 410 ml. of phosphorus oxychloride. The reaction mixture was worked up as described in Example 1 or 2. The crude cyclisation product was dissolved in ether, the solution was filtered and a solution of hydrogen chloride in ether was added to the filtrate. Crystals of 1-methyl-2-chloromethyl-5-(2'-thienyl)-1H-2,3-dihydro-1,4-benzodiazepine hydrochloride precipitated and were recrystallized from acetone/isopropanol. Melting point: 163°-164.5° C., yield: 98.3 g.

(B) 26.4 g. of the above hydrochloride were heated together with 10.4 g. of sodium azide in 100 ml. of dimethylformamide to 100° C. and maintained at this temperature for 3 hours. The dimethylformamide was then distilled off in vacuo, and the residue was taken up in 100 ml. of toluene and washed with saturated sodium chloride solution. After drying over sodium sulphate and filtration, the solvent was distilled in vacuo. 20.1 g. 1-methyl-2-azidomethyl-5-(2-thienyl)-1H-2,3-dihydro-1,4-benzodiazepine were obtained. IR spectrum, 2,120 $cm^{-1}$.

(C) 20.1 g. of the above azidomethyl compound were dissolved in 100 ml. of methanol, and, after the addition of 4.4 ml. of triethylamine and 10 ml. of hydrazine hydrate in 300 ml. of methanol, about 10 g. of Raney nickel were added in portions. After 4 hours, the catalyst was separated off, and the reaction solution was evaporated. The residue was dissolved in methylene chloride, and the solution was washed with saturated sodium chloride solution. 1-Methyl-2-aminomethyl-5-(2'-thienyl)-1H-2,3-dihydro-1,4-benzodizepine obtained after the customary working up was converted in a customary manner into the dihydrochloride. Melting point: 175° C. (with decomposition), yield: 16.6 g.

(D) 16.6 g. of the above dihydrochloride were dissolved, together with 20.5 ml. of triethylamine, in 400 ml. of methylene chloride and reacted with 7.3 ml. of thiophene-2-carboxylic chloride in a customary manner analagous to the procedure described in Example 1D or 2D, and after customary working up, the 1-methyl-2-[(thiophene-2-carbonyl)-aminomethyl]-1H-2,3-dihydro-1,4-benzodiazepine was obtained in the form of its hydrochloride. Melting point: 173°-197° C., yield: 6 g.

EXAMPLE 4

1-Methyl-2-[(furan-2-carbonyl)-aminomethyl]-5-(2'-thienyl)-1H-2,3-dihydro-1,4-benzodiazepine.

(A) 20.3 g. of 2-(2'-aminobenzoyl)thiophene were heated for 6 hours at 60°-70° C. together with 10.2 g. of epichlorohydrin and 6 g. of acetic acid. This reaction mixture was then poured onto water, and the mixture was extracted with methylene chloride. The organic phase was separated off, washed until neutral, dried and filtered, and the filtrate was evaporated. 25 g. of 2-(2'-[N-(3-chloro-2-hydroxylpropyl)-amino]-benzoyl)-thiophene were obtained as an oily crude product. This was heated without further purification, for 2.5 hours on a waterbath together with 32 ml. of formic acid and 16 ml. of 37% strength formaldehyde solution. The solution was then poured onto ice, and the mixture was extracted with chloroform. The organic phase was washed with saturated sodium carbonate solution until it had a neutral reaction. The chloroform phase was then dried and filtered, and the filtrate was evaporated. 24 g. of 2-(2'-[N-(3-chloro-2-hydroxypropyl)-methylamino]-benzoyl)-thiophene were obtained. This was reacted with 3.5 g. of sodium hydroxide and 6.8 ml. of water in 50 ml. of dioxane and 50 ml. of isopropanol for 10 hours at room temperature. After removal of the organic solvent in vacuo, the oily crude product was dissolved in methylene chloride, and the solution was washed with water until neutral, dried over sodium sulphate and filtered. The methylene chloride was distilled off, and 12 g. of 2-(2-[N-(2,3-epoxypropyl)-methylamino]-benzoyl)-thiophene were obtained. This was cyclised with 36 g. of ammonia in 1,200 ml. of methanol by heating for 10 hours at 150° C. in a steel autoclave. When the solvent had been distilled off, 9 g. of 1-methyl-3-hydroxy-6-thienyl-1,2,3,4-tetrahydro-1,5-benzodiazocine were obtained. Boiling for 2 hours with thionyl chloride under reflux produced 10 g. of crude 1-methyl-2-chloromethyl-5-(2'-thienyl)-1H-2,3-dihydro-1,4-benzodiazepine hydrochloride. After recrystallising from acetone/isopropanol, 8 g. of 1.methyl-2-chloromethyl-5-(2'-thienyl)-1H-2,3-dihydro-1,4-benzodiazepine hydrochloride having a melting point of 163°-164° C. were obtained.

(B) The above 2-chloromethyl compound was converted, as described in Example 3, into the corresponding 2-aminomethyl compound or the dihydrochloride thereof (melting point: 175° C. with decomposition).

(C) 1-Methyl-2-aminomethyl-5-(2'-thienyl)-1H-2,3-dihydro-1,4-benzodiazepine dihydrochloride obtained as above was reacted in the customary manner with furan-2-carboxylic chloride analogous to the reaction described in Example 2D. After customary working up, 1-methyl-2-[(furan-2-carbonyl)-aminomethyl]-5-(2-thienyl)-1H-2,3-dihydro-1,4-benzodiazepine hydrochloride was obtained. Melting point: 221°-225° C.

EXAMPLE 5

8-Methoxy-1-methyl-2-benzoylaminomethyl-5-(3'-thienyl)-1H-2,3-dihydro-1,4-benzodiazepine (A) 16 g. of 8-methoxy-1-methyl-2-azidomethyl-5-(3'-thienyl)-1H-2,3-dihydro-1,4-benzodiazepine (prepared from $N_1$-(thiophene-3-carbonyl)-$N_2$-methyl-$N_2$-(methoxyphenyl)-2-hydroxy-1,3-diaminopropane in a manner analogous to that described in Example 3A-B) were dissolved in 200 ml. of methanol, and 12 ml. of 1,3-dimercaptopropane and 16 ml. of triethylamine were added at room temperature. The reaction solution was stirred for 48 hours at room temperature. The solvent was then distilled off, and the residue was dissolved in 200 ml. of ether. The ethereal solution was filtered, and the filtrate was extracted with dilute hydrochloric acid (10%). Sodium hydroxide solution (20%) was added to the acidic, aqueous solution until the latter had an alkaline reaction. The solution was then extracted with ether. The ethereal solution was washed with saturated sodium chloride solution, dried over sodium sulphate and filtered, and the solvent was distilled from the filtrate. 9.9 g. of crude 8-methoxy-1-methyl-2-aminomethyl-5-(3'-thienyl)-1H-2,3-dihydro-1,4-benzodiazepine were obtained. It was possible to use the crude product without further purification for the reaction below. It was possible to convert the compound, in a customary manner, by treating it with hydrogen chloride dissolved in ether, into the dihydrochloride. Melting point of the dihydrochloride: 190°–211° C. (with decomposition).

(B) 9.5 g. of 8-methoxy-1-methyl-2-aminomethyl-5-(3'-thienyl)-1H-2,3-dihydro-1,4-benzodiazepine were dissolved with 3.2 g. of triethylamine in 120 ml. of methylene chloride. A solution of 4.9 g. of benzoyl chloride in 20 ml. of methylene chloride were then added dropwise to the solution while cooling with ice. The reaction solution was stirred for a further 2 hours at room temperature and thereafter washed with water, then with ammonia solution (10%) and again with water. After drying over sodium sulphate, it was filtered, and the solvent was distilled off in vacuo. 9 g. of crude 8-methoxy-1-methyl-2-benzoylaminomethyl-5-(3'-thienyl)-1H-2,3-dihydro-1,4-benzodiazepine were obtained as residue. The crude product was dissolved in a mixture of ether and ethyl acetate (1:1) The hydrochloride precipitated on addition of a solution of hydrogen chloride in ether. The hydrochloride was filtered off with suction and stirred with hot acetone. Yield: 7.3 g of hydrochloride, melting point: 233°–234° C.

EXAMPLE 6

1-Methyl-2-[(4'-trifluoromethylbenzoyl)-aminomethyl]-5-(3'-thienyl)-1H-2,3-dihydro-1,4-benzodiazepine.

(A) 10 g. of 1-methyl-2-azidomethyl-5-(3'-thienyl)-1H-2,3-dihydro-1,4-benzodiazepine (prepared from $N_1$-(thiophene-3-carbonyl)-$N_2$-methyl-$N_2$-phenyl-2-hydroxy-1,3-diaminopropane in a manner analogous to that described in Example 3A-B) were dissolved in 200 ml. of concentrated hydrochloric acid, and 20 g. of tin(II) chloride dihydrate were added at an internal temperature of 0°–3° C. The reaction mixture was stirred for 30 minutes while cooling with ice and then for 1 hour at room temperature. Further 10 g. amounts of tin(II) chloride dihydrate were then added at intervals of 2 hours. After 7 hours, the reaction solution was extracted with methylene chloride, and the methylene chloride phase was then washed with sodium hydroxide solution (20%), dried over sodium sulphate and filtered. The solvent was then distilled off in vacuo. 6.5 g. of crude 1-methyl-2-aminomethyl-5-(3'thienyl)-1H-2,3-dihydro-1,4-benzodiazepine were obtained as a residue.

(B) 6 g. of 1-methyl-2-aminomethyl-5-(3'-thienyl)-1H-2,3-dihydro-1,4-benzodiazepine were dissolved in 50 ml. of toluene. 4.4 g. of 4-trifluoromethylbenzoic acid were then added, and 7 g. of triethylamine were added after 30 minutes. A solution of 1.6 g. of phosphorus trichloride in 20 ml. of toluene was added dropwise with stirring to the reaction solution and the temperature increased to 40°–50° C. The reaction solution was heated for a further 1 hour at 80° C. and was then poured onto 500 ml. of water. The addition of concentrated sodium hydroxide solution established a pH value of 10. The organic phase was separated off, and the aqueous, alkaline phase was extracted once more with methylene chloride. The combined organic phases were worked up in a customary manner by washing them with water, drying over sodium sulphate and filtering, and by evaporating the filtrate. The hydrochloride was prepared in a customary manner from the crude 1-methyl-2-[(4'-trifluoromethylbenzoyl)-aminomethyl]-5-(3'-thienyl)-1H-2,3-dihydro-1,4-benzodiazepine obtained from the residue and crystallised from ethyl acetate. Yield: 7.5 g., melting point of the hydrochloride: 185°–188° C.

EXAMPLE 7

1-Methyl-2-[(4-cyanobenzoyl)-aminomethyl]-5-(3'-thienyl)-1H-2,3-dihydro-1,4-benzodiazepine 15.4 g. of 4-cyanobenzoic acid were dissolved in 300 ml. of methylene chloride, the solution was cooled down to 0°–5° C., and 14.6 ml. of triethylamine were added. 10 ml. of ethyl chloroformate were then added dropwise in the course of 5–10 minutes, and the reaction mixture was stirred for a further 30 minutes at a temperature of 0°–5° C. 28.5 g. of 1-methyl-2-aminomethyl-5-(3'-thienyl)-1H-2,3-dihydro-1,4-benzodiazepine (see example 1A-C for preparation), dissolved in 200 ml. of methylene chloride, were then added dropwise at such a rate that the temperature was maintained between 0° and 5° C. The reaction solution was then stirred for a further 4 hours at room temperature. The reaction mixture was then worked up in a customary manner. 37.6 g. of crude title compound were obtained and converted in a known manner into the hydrochloride. Melting point: 234°–239° C., yield: 31 g.

EXAMPLE 8

8-Methoxy-1-methyl-2-[(4'-cyanobenzoyl)-aminomethyl]-5-(3'-thienyl)-1H-2,3-dihydro-1,4-benzodiazepine 12.7 g. of 2-chloro-1-methylpyridinium iodide were suspended with stirring at room temperature in 350 ml. of methylene chloride, and 14 ml. of triethylamine and 9.5 g. of 4-cyanobenzoic acid were added to the suspension. After 15 minutes, a solution of 14.1 g. of 8-methoxy-1-methyl-2-aminomethyl-5-(3'-thienyl)-1H-2,3-dihydro-1,4-benzodiazepine (see Example 5A for preparation) in 50 ml. of methylene chloride was added dropwise in the course of 15 minutes. After a further 30 minutes, 300 ml. of water were added, and a small amount of aqueous ammonia solution (20%) was added to the mixture until it had a weakly alkaline reaction. After customary working up, 23.2 g. of crude title compound were obtained as a residue. This residue was chromatographed in succession with ether, methylene chloride and ethanol over 150 g. of silica gel. The resulting title base was converted in a known manner into the hydrochloride, which, after stirring with hot acetone, had a melting point of 256°–259° C. Yield: 17.3 g.

EXAMPLE 9

8-Methoxy-1-methyl-2-[(furan-3-carbonyl)-aminomethyl]-5-(3'-thienyl)-1H-2,3-dihydro-1,4-benzodiazepine 7.5 g. of 8-methoxy-1-methyl-2-aminomethyl-5-(3'-thienyl)-1H-2,3-dihydro-1,4-benzodiazepine (see Example 5A for preparation) were dissolved in 50 ml. of methylene chloride, and 10 ml. of a 2.5M solution of trimethylaluminium in n-hexane were added under nitrogen as an inert gas. The reaction solution was stirred for 15 minutes at room temperature. A solution of 3.5 g. of ethyl furan-3-carboxylate in 20 ml. of methylene chloride was then added dropwise. The reaction solution was heated for 50 hours at 35°–40° C. The reaction mixture was then separated into its components by the careful addition of a solution of ammonium chloride and sodium chloride in water, while cooling with ice. The resulting organic phase was separated off and washed several times with saturated sodium chloride solution. After customary working up, 7.3 g. of 8-methoxy-1-methyl-2-[(furan-3-carbonyl)-aminomethyl]-5-(3'-thienyl)-1H-2,3-dihydro-1,4-benzodiazepine hydrochloride were obtained. Melting point: 237°–238.5° C.

EXAMPLE 10

1-Methyl-2-[(thiophene-3-carbonyl)-aminomethyl]-5-(3'-pyridyl)-1H-2,3-dihydro-1,4-benzodiazepine (A) 107 ml. of epichlorohydrin were added dropwise with stirring to a warm solution at 60° C. of 123.5 g. of methyl N-methylanthranilate and 42.6 g. of glacial acetic acid. The mixture was stirred for a further 16 hours at 60° C., a further 17 ml. of epichlorohydrin were then added dropwise, and the mixture was stirred for a further 4 hours at 60° C. The reaction mixture was then cooled down to room temperature, poured onto ice/water and extracted with methylene chloride. The methylene chloride phase was washed with saturated sodium bicarbonate solution and water, dried over sodium sulphate and filtered, whereafter the filtrate was evaporated. 218 g. of crude N-methyl-N-(3-chloro-2-hydroxypropyl)-anthranilate were obtained as a residue.

(B) 218 g. of the ester obtained above were added to 1.5 l. of dry ether, and 51 g. of ground potassium hydroxide were added while cooling with ice. The mixture was stirred for 24 hours at room temperature. The solution was then decanted off and filtered, and the filtrate was evaporated. Crude 3-chloromethyl-1-methyl-1,2-dihydro-3H-5H-1,4-benzaxoxepine-5-one remaining in the residue was crystallised from ether, and the crystals were dried at 50° C. in vacuo. Yield: 54.8 g.

(C) 31.4 ml. of 3-bromopyridine were dissolved, with the exclusion of moisture, in 300 ml. of absolute ether, and the solution was cooled down to −50° C. 200 ml. of a 1.6M solution of n-butyllithium in hexane were slowly added dropwise under a nitrogen atmosphere, and the reaction mixture was then stirred for 40 minutes at −50° C. The 3-lithium pyridyl solution thus prepared was added dropwise at about −60° C. to a solution of 54.2 g. of the compound prepared under (B) in 4000 ml. of absolute tetrahydrofuran, and the reaction mixture was then stirred for 1 hour at −60° C. A solution of 20 ml. of water in 150 ml. of tetrahydrofuran was then slowly added dropwise at this temperature. The reaction mixture was allowed to warm to room temperature and was then diluted with about 200 ml. of toluene. The organic phase was separated off, washed with saturated sodium chloride solution, dried over sodium sulphate and filtered, and the filtrate was evaporated. 87 g. of crude product, which was purified by chromatography over 850 g. of silica gel using cyclohexane/ethyl acetate 3:7 as the eluent, remained as residue. 39.0 g. of 2-(2-[N-(3-chloro-2-hydroxypropyl)-methylamino]-benzoyl)-pyridine were obtained as an oil.

(D) 39 g. of the compound obtained above were dissolved in 314 ml. of dimethylformamide, and 32 g. of potassium phthalimide and 4.9 ml. of pyridine were added. The reaction mixture was stirred for 2 hours with the exclusion of moisture at a temperature of 120° C. The dimethylformamide was then distilled off, and the residue was taken up in water and methylene chloride. The organic phase was separated off, washed with water, dried over sodium sulphate and filtered, and the filtrate was evaporated. 51.0 g. of 2-(2-[N-(3-phthalimido-2-hydroxypropyl)-methylamino]-benzoyl)-pyridine remained as residue.

(E) 51.0 g. of the phthalimide compound obtained above were heated for 16 hours under reflux in 612 ml. of concentrated hydrochloric acid, during which period hydrogen chloride was passed from time to time into the reaction vessel. Hydrochloric acid was then largely drawn off, and the residue was taken up in water, rendered alkaline by means of dilute sodium hydroxide solution while cooling with ice, and extracted with methylene chloride. The organic phase was separated off, washed with saturated sodium chloride solution, dried over sodium sulphate and filtered, and the filtrate was evaporated. 29.8 g. of crude 2-(2-[N-(3-amino-2-hydroxypropyl)-methylamino]-benzoyl)-pyridine were obtained.

(F) 29.8 g. of the amine obtained above were heated for 8 hours at 90° C. in 259 ml. of toluene under a nitrogen atmosphere. The solution was cooled down to room temperature and filtered, and the filtrate was evaporated. 27.4 g. of 1-methyl-3-hydroxy-6-(2-pyridyl)-1,2,3,4-tetrahydro-1,5-benzodiazocine remained as a residue.

(G) 25.8 g. of the 3-hydroxybenzodiazocine compound obtained above were dissolved in 161 ml. of methylene chloride, and 190 ml. of carbon tetrachloride and 26.6 g. of triphenylphosphine were added. The reaction mixture was stirred for 3 hours under reflux, during which period after 1 hour a further 6.4 g. and after 1½ hours a further 1 g. of triphenylphosphine were added. The solvent was then distilled off and the residue was purified by chromatography over silica gel using as eluents firstly toluene, and secondly cyclohexane/ethyl acetate 4:6. 40 g. of crude product were obtained and taken up in 500 ml. of ether. This precipitated triphenylphosphine oxide as a white precipitate. The latter was removed by filtration with suction, and the solution was concentrated by evaporation. 23.3 g. of a mixture of 1-methyl-2-chloromethyl-5-(2-pyridyl)-1H-2,3-dihydro-1,4-benzodiazepine and 1-methyl-3-chloro-6-(2-pyridyl)-1,2,3,4-tetrahydro-1,5-benzodiazocine were obtained.

(H) Without separation or further purification, 25 g. of the above mixture were boiled under reflux with stirring for 6 hours in 205 ml. of methanol together with 18 g. of potassium phthalimide and 1.43 g. of potassium iodide, during which period after 2 hours a further 5 g. and after 5 hours a further 2 g. of potassium phthalimide were added. Methanol was then distilled off, the residue was taken up in water/methylene chloride, the organic phase was separated off, washed with water, dried over sodium sulphate and filtered, and the filtrate was evaporated. 27.5 g. of 1-methyl-2-phthalimido-5-(2-pyridyl)-1H-2,3-dihydro-1,4-benzodiazepine were obtained.

(I) 27.5 g. of the above 2-phthalimido-compound were heated for 2 hours under reflux in 325 ml. of ethanol together with 7.3 ml. of hydrazine hydrate and 35 ml. of concentrated hydrochloric acid. The ethanol was distilled off, dilute hydrochloric acid was added to the residue, and the solution was filtered under suction from the resulting precipitate whereafter the filtrate was extracted with methylene chloride. The aqueous phase was rendered alkaline by means of dilute sodium hydroxide solution while cooling with ice and then extracted with methylene chloride. The methylene chloride phase was washed with sodium chloride solution, dried over sodium sulphate and filtered, and the filtrate was evaporated. 12.8 g. of 1-methyl-2-aminomethyl-5-(2-pyridyl)-1H-2,3-dihydro-1,4-benzodiazepine were obtained.

(J) 4.2 g. of the amine obtained above were dissolved in 120 ml. of methylene chloride and 2.7 ml. of triethylamine. A solution of 2.5 g. of thiophene-3-carboxylic chloride in 5 ml. of methylene chloride was slowly added dropwise with stirring and while cooling with ice to this solution. Water was added to the reaction mixture; the methylene chloride phase was separated off, washed with dilute sodium hydroxide solution and with water, dried over sodium sulphate and filtered, and the filtrate was evaporated. 6.4 g. of crude product were obtained, which were purified by chromatography over 80 g. of alumina (activity level II/III) using toluene/methylene chloride as the eluent. 5.2 g. of 1-methyl-2-(thiophene-3-carbonyl)-aminomethyl-5-(2-pyridyl)-1H-2,3-dihydro-1,4-benzodiazepine were obtained. 5.2 g. of this base were dissolved in acetone, and a solution of 1.8 g. of fumaric acid in ethanol was added to the solution. The solution was concentrated by evaporation, and the residue was taken up in acetone. The difumarate of the title compound gradually precipitated in the form of crystals. The crystals were dried for 2 days at 60° C. in vacuo. Yield: 3.5 g., melting point: 175°–177° C.

By means of the processes described in Examples 1 to 10, it is also possible to obtain, by acylation of the corresponding 2-aminomethyl-5-heteroaryl-1H-2,3-dihydro-1,4-benzodiazepine compounds, the 2-acylaminomethyl-5-heteroaryl-1H-2,3-dihydro-1,4-benzodiazepine compounds listed in the Table II below.

| Example No. | $R_1$ | $R_2$ | n | $R_3$ | $R_4$ | $R_5$ | $R_6$ | Salt | m.p. in °C. |
|---|---|---|---|---|---|---|---|---|---|
| 11 | $CH_3$ | H | 0 | phen. | 3-thien. | H | H | HCl | 211–215 |
| 12 | $CH_3$ | H | 0 | 4-$CF_3$—phen. | 3-thien. | 8-$OCH_3$ | H | HCl | 243–246 |
| 13 | $CH_3$ | H | 0 | 3-thien. | 3-thien. | 8-$OCH_3$ | H | HCl | 234–236 |
| 14 | $CH_3$ | H | 0 | 2-thien. | 3-thien. | 7,8-$OCH_2O$ | | HCl | 267–273 |
| 15 | $CH_3$ | H | 0 | 2-fur. | 3-thien. | 7,8-$OCH_2O$ | | HCl | 256–265 |
| 16 | $CH_3$ | H | 0 | 3-fur. | 3-thien. | 7,8-$OCH_2O$ | | HCl | 274–277 |
| 17 | $CH_3$ | H | 0 | 3-thien. | 3-thien. | 7,8-$OCH_2O$ | | HCl | 276–283 |
| 18 | $CH_3$ | H | 0 | phen. | 3-thien. | 7,8-$OCH_2O$ | | HCl | 264–270 |
| 19 | $CH_3$ | H | 0 | 3-CN—phen. | 3-thien. | 7,8-$OCH_2O$ | | HCl | 246–258 |
| 20 | $CH_3$ | H | 0 | 4-$CH_3O$—phen. | 3-thien. | 7,8-$OCH_2O$ | | HCl | 270–276 |
| 21 | $CH_3$ | H | 0 | 4-CN—phen. | 3-thien. | 7,8-$OCH_2O$ | | HCl .0,2 $C_2H_5OH$ | 271–279 |
| 22 | $CH_3$ | H | 0 | 4-$NO_2$—phen. | 3-thien. | 7,8-$OCH_2O$ | | HCl | 266–271 |
| 23 | $CH_3$ | H | 2 | phen. | 3-thien. | 7,8-$OCH_2O$ | | HCl | 193–198 |
| 24 | $CH_3$ | H | 0 | 2-pyrid. | 3-thien. | 7,8-$OCH_2O$ | | 1,8 HCl.1 $H_2O$ | 204–212(D) |
| 25 | $CH_3$ | H | 1 | 3-pyrid. | 3-thien. | 7,8-$OCH_2O$ | | HCl.0,1($CH_3)_2CO$ .0,7 $H_2O$ | 154–166(D) |
| 26 | $CH_3$ | H | 0 | 2-pyrrol. | 3-thien. | 7,8-$OCH_2O$ | | Base | 216–222 |
| 27 | $CH_3$ | H | 0 | 4-CN—phen. | 2-thien. | 7-$CH_3O$ | H | HCl | 252–257 |
| 28 | $CH_3$ | H | 1 | N—$CH_3$—4-$CH_3$—2-pyrrol. | 3-thien. | 7,8-$OCH_2O$ | | Base, am | 82–88 |
| 29 | $CH_3$ | H | 1 | 4-$CF_3$—phen. | 3-thien. | H | H | HCl | 202–205 |
| 30 | $CH_3$ | H | 1 | 2-$CF_3$—phen. | 3-thien. | H | H | HCl | 225–228 |
| 31 | $CH_3$ | H | 0 | 5-$CH_3$—2-thien. | 3-thien. | H | H | HCl | 216–222 |
| 32 | $CH_3$ | H | 0 | 2-$CH_3O$—4-Cl—phen. | 3-thien. | H | H | HCl | 184–187 |
| 33 | $CH_3$ | H | 1 | 4-Cl—phen. | 3-thien. | H | H | HCl | 200–203 |
| 34 | $CH_3$ | H | 0 | 2-Cl—3-pyrid. | 3-thien. | H | H | 2HCl | 190–195 |
| 35 | $CH_3$ | H | 0 | N—$CH_3$—5-$CH_3$—2-pyrrol. | 3-thien. | H | H | Base | 90 |
| 36 | $CH_3$ | H | 2 | 4-$CH_3O$—phen. | 3-thien. | H | H | Base | Oil |
| 37 | $CH_3$ | H | 0 | 3,4-di-Cl—phen. | 3-thien. | H | H | HCl | 209–211 |
| 38 | $CH_3$ | H | 0 | phen. | 3-thien. | 7-$CH_3O$ | H | HCl | 197–203 |
| 39 | $CH_3$ | H | 0 | 4-CN—phen. | 3-thien. | 7-$CH_3O$ | H | HCl | 208–212 |
| 40 | $CH_3$ | H | 0 | 3-thien. | 3-thien. | 7-$CH_3O$ | H | Base | 157–162 |
| 41 | $CH_3$ | H | 0 | phen. | 3-thien. | 7-F | H | Base | 142–145 |
| 42 | $CH_3$ | H | 0 | 4-CN—phen. | 3-thien. | 7-F | H | Base | 173 |
| 43 | $CH_3$ | H | 0 | 3-fur. | 3-thien. | 7-F | H | HCl | 220–225 |
| 44 | $CH_3$ | H | 0 | 2-Cl—phen. | 3-thien. | 7-F | H | HCl | 223–227 |
| 45 | $CH_3$ | H | 0 | phen. | 3-thien. | 7-Cl | H | HCl | 193–196 |
| 46 | $CH_3$ | H | 1 | phen. | 3-thien. | 7-Cl | H | Base | Oil |
| 47 | $CH_3$ | H | 0 | 2-Cl—phen. | 3-thien. | 7-Cl | H | HCl | 214–217 |
| 48 | $CH_3$ | H | 0 | 3-Cl—phen. | 3-thien. | 7-Cl | H | HCl.0,25 ($CH_3)_2CHOH$ | 204–207 |
| 49 | $CH_3$ | H | 1 | 3-Cl—phen. | 3-thien. | 7-Cl | H | HCl.0,25 $H_2O$ am | 132–137 |
| 50 | $CH_3$ | H | 1 | 2-Cl—phen. | 3-thien. | 7-Cl | H | HCl.0,1 ($CH_3)_2CHOH$ | 187–191 |
| 51 | $CH_3$ | H | 0 | 4-$NO_2$—phen. | 3-thien. | 7-Cl | H | Base 0,1 HCl | 197 |
| 52 | $CH_3$ | H | 0 | 4-CN—phen. | 3-thien. | 7-Cl | H | 1,2 HCl | 235–240 |
| 53 | $CH_3$ | H | 0 | 4-F—phen. | 3-thien. | 7-Cl | H | HCl | 235–238 |

-continued

| Example No. | R₁ | R₂ | n | R₃ | R₄ | R₅ | R₆ | Salt | m.p. in °C. |
|---|---|---|---|---|---|---|---|---|---|
| 54 | CH₃ | H | 0 | 3-fur. | 3-thien. | 7-Cl | H | HCl | 227–230 |
| 55 | CH₃ | H | 0 | 3-thien. | 3-thien. | 7-Cl | H | HCl | 205–209 |
| 56 | CH₃ | H | 1 | 3-thien. | 3-thien. | 7-Cl | H | HCl | 184–187 |
| 57 | CH₃ | H | 0 | 2-pyrid. | 3-thien. | 7-Cl | H | Base | Oil |
| 58 | CH₃ | H | 0 | phen. | 3-thien. | 8-CH₃ | H | HCl | 207–211 |
| 59 | CH₃ | H | 1 | phen. | 3-thien. | 8-CH₃ | H | HCl | 184–190 |
| 60 | CH₃ | H | 0 | 4-CN—phen. | 3-thien. | 8-CH₃ | H | HCl.0,5 H₂O | 152–156 |
| 61 | CH₃ | H | 2 | phen. | 3-thien. | 8-CH₃ | H | HCl.0,3 (CH₃)₂CHOH am | 129–134 |
| 62 | CH₃ | H | 0 | 4-F—phen. | 3-thien. | 8-CH₃ | H | HCl | 218–222 |
| 63 | CH₃ | H | 0 | 2-Cl—phen. | 3-thien. | 8-CH₃ | H | HCl.0,25 H₂O | 208–211 |
| 64 | CH₃ | H | 1 | 2-Cl—phen. | 3-thien. | 8-CH₃ | H | HCl am | 108–112 |
| 65 | CH₃ | H | 0 | 3-thien. | 3-thien. | 8-CH₃ | H | 1,05 HCl .0,5 H₂O | 216–220 |
| 66 | CH₃ | H | 0 | 3-fur. | 3-thien. | 8-CH₃ | H | HCl | 212–216 |
| 67 | CH₃ | H | 0 | 4-NO₂—phen. | 3-thien. | 8-CH₃ | H | HCl | 159–162 |
| 68 | CH₃ | H | 0 | 2-pyrid. | 3-thien. | 8-CH₃ | H | HCl.0,4 H₂O am | 136–138 |
| 69 | CH₃ | H | 1 | 3-thien. | 3-thien. | 8-CH₃ | H | Base | Oil |
| 70 | CH₃ | H | 0 | 4-CH₃O—phen. | 3-thien. | 8-CH₃ | H | HCl | 233–236 |
| 71 | H | H | 0 | 4-CN—phen. | 3-thien. | 8-F | H | 1,2 HCl.0,25 H₂O, am | 131–135 |
| 72 | CH₃ | H | 0 | 4-CN—phen. | 3-thien. | 8-F | H | HCl | 212–216 |
| 73 | CH₃ | H | 0 | phen. | 3-thien. | 8-F | H | HCl | 199–203 |
| 74 | CH₃ | H | 0 | 4-CF₃—phen. | 3-thien. | 8-F | H | HCl | 205–209 |
| 75 | CH₃ | H | 0 | 3-fur. | 3-thien. | 8-F | H | Base | Oil |
| 76 | H | H | 0 | phen. | 3-thien. | 8-F | H | Base | Oil |
| 77 | C₂H₅ | H | 0 | 4-CN—phen. | 3-thien. | 8-F | H | HCl | 201–205 |
| 78 | n-C₃H₇ | H | 0 | 3-fur. | 3-thien. | 8-F | H | Base | Oil |
| 79 | n-C₄H₉ | H | 0 | 4-CN—phen. | 3-thien. | 8-F | H | HCl.0,2 (CH₃)₂CHOH | 179–183 |
| 80 | CH₃ | H | 0 | 4-F—phen. | 3-thien. | 8-F | H | HCl | 197–201 |
| 81 | CH₃ | H | 0 | 3-thien. | 3-thien. | 8-OC₂H₅ | H | HCl | 211–214 |
| 82 | CH₃ | H | 0 | 4-CH₃O—phen. | 3-thien. | 8-OC₂H₅ | H | HCl | 200–204 |
| 83 | CH₃ | H | 0 | phen. | 3-thien. | 8-OC₂H₅ | H | Base | Oil |
| 84 | CH₃ | H | 0 | 4-CN—phen. | 5-Cl—2-thien. | H | H | HCl | 221–232 |
| 85 | CH₃ | H | 0 | 3-fur. | 5-Cl—2-thien. | H | H | HCl | 215–227 |
| 86 | CH₃ | H | 0 | 4-CN—phen. | 4-Br—2-thien. | H | H | HCl | 255–258 |
| 87 | CH₃ | H | 0 | 3-fur. | 3-CH₃—2-thien. | H | H | HCl | 234–238 |
| 88 | CH₃ | H | 0 | phen. | 3-CH₃—2-thien. | H | H | HCl | 257–259 (D) |
| 89 | CH₃ | H | 0 | 4-CN—phen. | 3-CH₃—2-thien. | H | H | HCl | 157–160 |
| 90 | CH₃ | H | 0 | phen. | 5-CH₃—2-thien. | 8-CH₃ | H | HCl | 227–230 |
| 91 | CH₃ | H | 0 | 4-CN—phen. | 5-CH₃—2-thien. | 8-CH₃ | H | HCl | 207–211 |
| 92 | CH₃ | H | 0 | 4-NO₂—phen. | 5-CH₃—2-thien. | 8-CH₃ | H | HCl | 191–197 |
| 93 | CH₃ | H | 0 | 2-Cl—phen. | 5-CH₃—2-thien. | 8-CH₃ | H | HCl | 204–206 |
| 94 | CH₃ | H | 1 | 3-thien. | 5-CH₃—2-thien. | 8-CH₃ | H | HCl | 233–235 |
| 95 | CH₃ | H | 0 | 3-fur. | 5-CH₃—2-thien. | 8-CH₃ | H | Base | 183–185 |
| 96 | CH₃ | H | 0 | 4-CH₃O—phen. | 3-Cl—2-thien. | H | H | HCl.0,5 H₂O | 209–216 |
| 97 | CH₃ | H | 0 | 3-fur. | 3-Cl—2-thien. | 8-CH₃ | H | HCl | 236–246 |
| 98 | CH₃ | H | 0 | 4-CN—phen. | 3-Cl—2-thien. | 8-CH₃ | H | HCl | 216–219 |
| 99 | CH₃ | H | 2 | phen. | 5-CH₃—2-thien. | 8-CH₃ | H | HCl.0,35 H₂O | 125 (S) |
| 100 | CH₃ | H | 0 | N—CH₃—2-pyrrol. | 5-CH₃—2-thien. | 8-CH₃ | H | HCl.0,5 H₂O | 175 |
| 101 | CH₃ | H | 0 | 2-thien. | 2-fur. | H | H | HCl | 173–176 |
| 102 | CH₃ | H | 0 | phen. | 2-fur. | 8-CH₃O | H | HCl | 218–227 |
| 103 | CH₃ | H | 0 | phen. | 2-fur. | H | H | HCl | 201–203 |
| 104 | CH₃ | H | 0 | 3-fur. | 2-fur. | H | H | HCl.0,5 H₂O | 150 (S) |
| 105 | CH₃ | H | 0 | 3-CN—phen. | 2-fur. | H | H | HCl.0,6 H₂O | 165 (S) |
| 106 | CH₃ | H | 0 | 4-CN—phen. | 2-fur. | H | H | 1,7 HCl .0,7 H₂O | 180 (S) |
| 107 | CH₃ | H | 0 | 3-fur. | 3-fur. | 8-CH₃O | H | HCl | 236–239 |
| 108 | CH₃ | H | 0 | 3-fur. | 3-fur. | 8-CH₃ | H | HCl | 244–252 |
| 109 | CH₃ | H | 0 | phen. | 3-fur. | 8-CH₃ | H | HCl | 228–235 |
| 110 | CH₃ | H | 0 | 3-thien. | 3-fur. | 8-CH₃ | H | HCl | 236–238 |
| 111 | CH₃ | H | 0 | 4-CN—phen. | 3-fur. | 8-CH₃ | H | HCl.0,3 H₂O | 259–261 |
| 112 | CH₃ | H | 0 | 3-CN—phen. | 3-fur. | 8-CH₃ | H | HCl | 193–195 |
| 113 | CH₃ | H | 0 | 3-fur. | 3-fur. | 8-CH₃O | H | HCl | 236–239 |
| 114 | CH₃ | H | 0 | phen. | 3-fur. | 8-CH₃O | H | HCl | 240–242 |
| 115 | CH₃ | H | 0 | 4-CF₃—phen. | 3-fur. | 8-CH₃O | H | HCl | 240–244 |
| 116 | CH₃ | H | 0 | 4-CH₃—phen. | 3-fur. | H | H | HCl | 238–240 |
| 117 | CH₃ | H | 0 | 4-CH₃O—phen. | 3-fur. | H | H | Base | Oil |
| 118 | CH₃ | H | 1 | 2-Cl—phen. | 3-fur. | 8-CH₃O | H | HCl | 152–156 |
| 119 | CH₃ | H | 0 | 3-fur. | 3-fur. | H | H | HCl | 222–225 |
| 120 | CH₃ | H | 0 | 4-CN—phen. | 3-fur. | H | H | HCl | 173–178 (S) |
| 121 | CH₃ | H | 0 | phen. | 3-fur. | H | H | HCl | 235–237 |
| 122 | CH₃ | H | 0 | 3-fur. | 2-pyrid. | H | H | Base | 143–145 |
| 123 | CH₃ | H | 1 | 2-Cl—phen. | 2-pyrid. | H | H | p-Tos.0,3 H₂O | 132–135 |
| 124 | CH₃ | H | 0 | 4-CN—phen. | 2-pyrid. | H | H | p-Tos.0,25 H₂O | 201–204 |
| 125 | CH₃ | H | 0 | 4-CN—phen. | 3-pyrid. | H | H | p-Tos | 199–201 |
| 126 | CH₃ | H | 0 | 3-fur. | 3-pyrid. | H | H | di-Fum | 154–157 |
| 127 | CH₃ | H | 1 | 2-Cl—phen. | 4-pyrid. | 8-CH₃O | H | 2,25 Mal | 176–178 |

-continued

| Example No. | $R_1$ | $R_2$ | n | $R_3$ | $R_4$ | $R_5$ | $R_6$ | Salt | m.p. in °C. |
|---|---|---|---|---|---|---|---|---|---|
| 128 | $CH_3$ | H | 0 | 4-CN—phen. | 4-pyrid. | 8-$CH_3O$ | H | Base | Oil |
| 129 | $CH_3$ | H | 0 | 3-fur. | 4-pyrid. | 8-$CH_3O$ | H | Base | Oil |
| 130 | $CH_3$ | H | 0 | phen. | 2-pyrid. | 7-$CH_3$ | H | Base | Oil |
| 131 | $CH_3$ | H | 0 | 3-fur. | 2-pyrid. | 7-$CH_3$ | H | Base | Oil |
| 132 | $CH_3$ | H | 0 | phen. | N—$CH_3$—2-pyrrol. | H | H | p-Tos | 180–182 |
| 133 | $CH_3$ | H | 1 | 2-Cl—phen. | N—$CH_3$—2-pyrrol. | H | H | Base | 135–136 |
| 134 | $CH_3$ | H | 0 | phen. | N—$CH_3$—3-pyrrol. | H | H | Base am | 93–98 |
| 135 | $CH_3$ | H | 0 | phen. | 3-pyrrol. | H | H | Base | Oil |
| 136 | $CH_3$ | H | 0 | phen. | 2-thien. | 7-$CH_3O$ | H | 1,1 HCl .0,4 $H_2O$ | 202–205 |
| 137 | $CH_3$ | H | 0 | 3-fur. | 2-thien. | 7-$CH_3O$ | H | 1,3 HCl .0,5 $H_2O$ | 143–158 |
| 138 | $CH_3$ | H | 0 | 4-$CH_3O$—phen. | 3-thien. | 8-F | H | Base | Oil |
| 139 | $CH_3$ | H | 0 | phen. | 3-thien. | 7-$CH_3$ | 8-F | HCl.0,2 $H_2O$ .0,1($CH_3$)$_2$CHOH | 183–187 |
| 140 | $CH_3$ | H | 0 | 3,4-$OCH_2O$—phen. | 3-thien. | 7-$CH_3$ | 8-F | HCl | 197–201 |
| 141 | $CH_3$ | H | 0 | 3,4-$OCH_2O$—phen. | 3-thien. | 7-F | 8-$CH_3$ | HCl | 212–218 |
| 142 | $CH_3$ | H | 0 | 4-OH—phen. | 3-thien. | 7-$CH_3O$ | H | 1,1 HCl .0,1 $H_2O$ | 193–197 |
| 143 | $CH_3$ | H | 0 | 4-$CH_3COO$—phen. | 3-thien. | 7-$CH_3O$ | H | Base | Oil |
| 144 | $CH_3$ | H | 0 | 4-$NH_2$—phen. | 3-thien. | 7-Cl | H | 1,85 HCl.0.5 $H_2O$ am | 112–116 |
| 145 | $CH_3$ | H | 0 | 4-$CH_3CONH$—phen. | 3-thien. | 7-Cl | H | 1,05 HCl.0,25 $H_2O$ | 178–182 |
| 146 | $CH_3$ | H | 0 | 4-$(CH_3)_2N$—phen. | 3-thien. | 7-Cl | H | 1,9 HCl.0,45 $H_2O$ am | 122–128 |
| 147 | $CH_3$ | H | 1 | 4-F—phen. | 3-thien. | H | H | HCl | 223–229 |
| 148 | $CH_3$ | H | 1 | 2-F—phen. | 3-thien. | H | H | HCl | 198–200 |
| 149 | $CH_3$ | H | 1 | 2-F—phen. | 3-thien. | 7,8-$OCH_2O$ | | HCl | 227–234 |
| 150 | $CH_3$ | H | 0 | phen. | N—$CH_3$—3-pyrrol. | 8-$OCH_3$ | H | Base | Oil | phen. = phenyl
fur. = furyl
thien. = thienyl
pyrrol. = pyrrolyl
pyrid. = pyridyl
HCl = hydrochloride
Base = free base
p-Tos. = p-toluenesulphonate
Fum = fumarate
Mal = maleinate
(D) = decomposition
(S) = sintering
am = amorphous The invention will now be further illustrated by the following Examples of pharmaceutical compositions containing the compounds of formula I.

EXAMPLE I: Tablets

Tablets are prepared with the following composition per tablet:

| | |
|---|---|
| 1-Methyl-2-[(furan-2-carbonyl)-aminomethyl]-5-(2'-furyl)-1H—2,3-dihydro-1,4-benzodiazepine hydrochloride as active compound | 25 mg. |
| Cornstarch | 60 mg. |
| Lactose | 130 mg. |
| Gelatine (10% solution) | 6 mg. |

The active compound, cornstarch and lactose are thickened with a 10% strength gelatine solution. The paste is triturated and the granules obtained are placed on a suitable sheet and dried at 45° C. The dried granules are passed through a trituration machine and fed to a mixer where the following substances are added:

| | |
|---|---|
| Talc | 5 mg. |
| Magnesium stearate | 5 mg. |
| Cornstarch | 9 mg. |

The resulting mixture is then compressed to form tablets each weighing 240 mg.

EXAMPLE II: Suppositories

Suppositories with the following composition are prepared:

| | |
|---|---|
| 1-Methyl-2-[(thiophene-3-carbonyl)-aminomethyl]-5-(3-thienyl)-1H—2,3-dihydro-1,4-benzodiazepine as active compound | 25 mg. |
| Cocoa butter as supporting base | 1,975 mg. |

The active compound and the finely ground suppository base are thoroughly mixed and then melted. Suppositories each weighing 2 g. are cast from the melt which is kept homogeneous by stirring.

EXAMPLE III: Injection solution

A solution for parenteral use is prepared with the following components:

| | |
|---|---|
| 1-Methyl-2-[(thiophene-3-carbonyl)-aminomethyl]-5-(3-thienyl)-1H—2,3-dihydro-1,4-benzodiazepine as active compound | 10% |
| Dimethyl acetamide | 10% |
| Propylene glycol | 50% |
| Benzylalcohol | 1.5% |
| Ethanol | 10% |
| Water for injection to | 100%. |

The active compound is dissolved in the dimethyl acetamide and then mixed with the benzylalcohol, propylene glycol, ethanol and water. The resulting mixture is filtered through a tube filter, filled into suitable ampoules, sealed and sterilised.

The foregoing description and examples have been set forth merely to illustrate the invention and are not intended to be limiting. Since modifications of the disclosed embodiments incorporating the spirit and substance of the invention may occur to persons skilled in the art, the scope of the invention is to be limited solely with respect to the appended claims and equivalents.

What is claimed is:

1. A 2-azidomethyl-1H-2,3-dihydro-1,4-benzodiazepine compound corresponding to the general formula IV

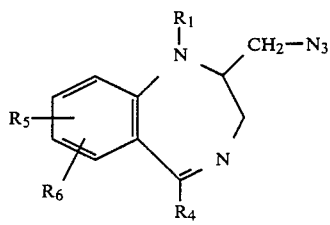

wherein $R_1$ is hydrogen, lower alkyl, lower alkenyl or cyclopropylmethyl;

$R_4$ is

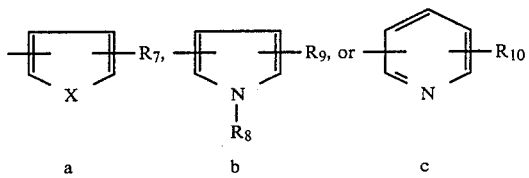

wherein

X is oxygen or sulphur;

$R_7$ is hydrogen, halogen, lower alkyl, lower alkoxy or nitro;

$R_8$ is hydrogen or lower alkyl;

$R_9$ is hydrogen or lower alkyl;

$R_{10}$ is hydrogen, chlorine or lower alkyl;

$R_5$ is hydrogen, halogen, lower alkyl, lower alkoxy, hydroxyl, lower alkylthio, nitro, trifluoromethyl, cyano, amino, lower mono- or dialkylamino, lower monoalkylanoylamino, lower N-alkyl-N-alkanoylamino or lower alkanoyloxy; and $R_6$ is hydrogen, halogen, lower alkyl, or lower alkoxy; or $R_5$ and $R_6$ are bonded to adjacent carbon atoms and together denote methylenedioxy or ethylenedioxy;

and the optical isomers and acid addition salts of said compound.

* * * * *